United States Patent [19]

Trivedi et al.

[11] 4,109,094

[45] Aug. 22, 1978

[54] METHOD FOR QUATERNIZING IMIDAZOLINES

[75] Inventors: Bhupendra C. Trivedi, Worthington; Robert A. Grimm, Columbus; R. B. McConnell, Dublin, all of Ohio

[73] Assignee: Ashland Oil, Inc., Ashland, Ky.

[21] Appl. No.: 809,988

[22] Filed: Jun. 27, 1977

[51] Int. Cl.$^2$ ............................................. C07D 233/16
[52] U.S. Cl. ...................................... 548/347; 548/354
[58] Field of Search .................................. 548/354, 347

[56] References Cited

U.S. PATENT DOCUMENTS

| | | | |
|---|---|---|---|
| 2,971,006 | 2/1961 | Mayhew et al. | 548/354 |
| 3,146,267 | 8/1964 | Weinstein et al. | 548/354 |
| 3,849,435 | 11/1974 | Diery et al. | 548/354 |

*Primary Examiner*—Henry R. Jiles
*Assistant Examiner*—Jane T. Fan

[57] ABSTRACT

Method for exhaustively alkylating the amine content of an imidazoline product prepared from a higher fatty acid and a dialkylene triamine wherein the protonated species formed in the course of the alkylation reaction are repeatedly neutralized, followed in each instance by reaction with an essentially equivalent amount of the alkylating agent based on the free amine present until the starting amine content of said product is predominantly converted to quaternary ammonium derivatives.

4 Claims, No Drawings

METHOD FOR QUATERNIZING IMIDAZOLINES

BACKGROUND OF THE INVENTION

1. Field of the Invention

This invention relates to a method for quaternizing an amine mixture consisting essentially of disubstituted imidazolines.

2. Description of the Prior Art

Quaternary ammonium salts of compounds containing the imidazoline ring structure and further substituted in the No. 1 and 2 positions with a long chain acyclic group are recognized for their effectiveness as fabric softeners. As a matter of fact, the bulk of the currently marketed fabric softeners are of this type.

The foregoing imidazoline compounds are prepared by first condensing a higher fatty acid with a dialkylene triamine containing a secondary amine group in a gamma position with respect to at least one of the terminal primary amine groups. This condensation reaction, upon employing an appropriate amount of the fatty acid, leads to the formation of the corresponding diamidoamine which is thereupon cyclized to yield the indicated substituted imidazoline structure.

Following cyclization, the product is quaternized to provide the quaternary ammonium salts thereof using any of the known quaternizing agents for this purpose. In the commercial production of imidazolines of the foregoing type, it is not feasible from a practical standpoint to achieve complete cyclization of the amidoamine intermediate. About 92% conversion is the best that can be realized in such an operation and the inability to obtain complete cyclization presents problems in preparing the quaternary ammonium derivatives thereof.

As indicated, the cyclization product will normally contain from 8–10% primary and secondary amines. It is not feasible to exhaustively alkylate said amines in accordance with conventional quaternization practices insofar as they are prone to form mainly acid salts and thus remain as such in the final product as impurities since these compounds are devoid of fabric softening properties. Beyond this, these impurities tend to react with dyes and perfumes ordinarily present in household softening formulations thereby adversely altering the nature of these additives. In addition, there is evidence that during a quaternization procedure some of the imidazoline compounds are trapped as an acid salt by amine exchange and consequently do not react with the quaternizing agent.

The object of the present invention is accordingly that of providing a procedure for alkylating imidazoline products containing free primary and secondary amines to achieve a quaternized product having a substantially reduced amount of unquaternized imidazoline and impurities in the form of the acid salts of said primary and secondary amines.

SUMMARY OF THE INVENTION

In accordance with the present invention, a method is provided for exhaustively alkylating an imidazoline product containing primary and secondary amines in the order of about 10% resulting from the incomplete cyclization of a diamidoamine prepared by condensing an ethylene-alkylene triamine and a higher fatty acid. The method involves a repetitive sequence of quaternization and subsequent neutralization of the protonated species formed in the course of the quaternization reaction. In each sequence of the indicated operations following the initial sequence, wherein the quaternizing agent is employed on a basis of about 1 mole thereof per mole of the starting diamidoamine condensate, the amount of quaternizing agent added is about equivalent to the amount of the base used in the prior neutralization step. The sequence of quaternizing and neutralizing in this manner is continued until the non-quaternized content of the reaction mixture is less than about 3 weight percent.

DESCRIPTION OF THE PREFERRED EMBODIMENTS

The preparation of imidazoline compounds of the type concerned herein basically involves the reaction of a higher fatty acid or functional equivalent thereof with a dialkylene triamine. As previously mentioned, suitable polyamines for this purpose are those containing a secondary amine group in a gamma position with respect to at least one of the terminal primary amine groups. Representative of such amines which are commercially available are diethylene triamine and ethylene-propylene triamine.

With respect to the applicable fatty acid reactants, the $C_8$–$C_{24}$ saturated or unsaturated fatty acids are suitable for deriving the contemplated imidazoline compounds. The preferred fatty acids from the standpoint of preparing quaternary derivatives exhibiting optimum softening properties are those derived from tallow. The tallow can be employed as such or it can by hydrogenated. Since the natural occuring glyceride form of the indicated animal and vegetable acids are more economical than the free acids or the mono esters thereof, it is customarily preferred to use these fatty acids in this form.

In effecting the initial condensation of the fatty acids and the triamine such are merely heated at about 100° to 200° C. preferably employing a nitrogen sparge when the fatty acids are in the form of the free acid or mono ester thereof. In the case of using the triglyceride of the fatty acids, it is preferred to carry out the condensation at a slight pressure. The fatty acids and triamines are reacted on the basis of 2 moles of the carboxylic acids per mole of the polyamine. Of course, when the triglyceride form of the fatty acids are used one will employ two-thirds of a mole thereof to 1 mole of the polyamine. Where a triglyceride is used, splitting to effect the in situ formation of the polyamidoamine is readily accomplished in the reaction system concerned. The reaction can be maintained under reduced pressure in order to assist in removal of the water condensation; however, sparging under atmospheric pressures will serve the same purpose.

The next step in deriving the imidazoline compounds involves cyclizing the diamidoamine condensation product. This reaction is accomplished by heating the diamidoamine at a temperature between about 125° and 250° C. under vacuum. Reduced pressure conditions in the order of from 1 to 200 mm Hg suffice for this purpose. In the instances where the free fatty acids or a lower alkyl ester thereof is employed as a reactant, the use of moderate vacuum in the order indicated is generally observed. Where, however, the diamidoamine is derived from a triglyceride ester, it is advantageous to operate at the low levels of the indicated pressure range in order to effect the removal of the glycerin. The extent of cyclization can be noted by analyzing for the tertiary amine content. When this value holds constant the cyclization reaction is completed. As previously mentioned, cyclized products of this type contain a maximum of about 92% of imidazoline compounds.

The quaternization of the cyclized product in accordance with this invention can be carried out in a conventional manner. Generally, it is desirable to conduct the quaternization reaction by having the imidazoline product in the form of a concentrated dispersion thereof in an inert organic solvent. Suitable inert solvents include the various alkanols and glymes. Isopropanol is especially preferred for this purpose. The inert solvents should be anhydrous insofar as the presence of water tends to promote hydrolysis of the imidazoline structure. The quaternization reaction is best conducted by adding the quaternizing agent slowly to the imidazoline concentrate with stirring. The solids content of the concentrate for effecting this reaction can range from about 50 to 90 wt. percent but more usually is about 65% to 85% on a weight basis. Temperatures suitable for this purpose range from room temperature to about 125° C. depending upon the volatility characteristics of the inert solvent employed.

A variety of quaternizing agents are useful for preparing the quaternary ammonium salts. An exemplary enumeration thereof include: the lower alkyl chloride and bromides, e.g. methyl chloride; the di-lower alkyl sulfates; the trialkyl phospates and benzyl chloride or bromide. The di-lower alkyl sulfates, particularly dimethyl sulfate, represent the preferred quaternizing agents.

In accordance with the present invention, the cylcized product is first reacted as outlined above with the quaternizing agent on the basis of about one mole thereof per mole of the starting diamidoamine condensate. Next, the quaternized reaction mixture is neutralized employing an alkai metal alkoxide, preferably sodium methylate, as the base. Following neutralization, an additional amount of the quaternizing agent is added to the reaction mixture such being in the order of that equal to the equivalents of the base needed for neutralization. The sequence of quaternization and neutralization as aforesaid is repeated until the non-quaternized content of the reaction mixture is less than about 3 weight percent. The neutralization steps can be effected in two ways. The preferred mode consists of maintaining the reaction mixture at a relatively constant pH in the range of about 8-10. The other procedure is to permit the quaternization phase of any one sequence to run its course thereby providing a reaction mixture having a pH of about 5 which is then neutralized before an additional amount of the agent is added. Both of the aforedescribed modes are exemplified in the working examples to follow.

Although the preferred quaternary ammonium compounds prepared in accordance with this invention, especially those wherein the quaternizing anion is methyl sulfate, find particular utility in fabric softening applications, other important uses are indicated. For example, these quaternized products can be advantageously used in rinsing compositions for human hair, as an emulsifier for preparing oil and water emulsions, including bituminous or asphaltic materials, and as an anti-static agent for paper, fabric, polish, etc.

In order to illustrate to those skilled in the art the best mode contemplated for the implementation of the present invention, the following working examples are given. All parts are parts by weight unless otherwise stated.

EXAMPLE 1

The crude imidazoline samples used in this example and the succeeding example were prepared from hydrogenated tallow and diethylene triamine in accordance with the procedure generally outlined above. A mixture containing 300.7 parts of the crude imidazoline and 65.1 parts of isopropyl alcohol (IPA) was heated to 55°-60°C. with stirring until uniform, whereupon 61.9 parts of dimethyl sulfate (DMS) was added slowly and uniformly with stirring over 1 hour while maintaining a temperature within the indicated range. After an additional 30 minutes, an aliquot was analyzed to determine the amount of sodium methylate necessary to adjust the pH of the total mixture to about 7.0. Following analysis, 4.0 parts of a 25% solution of the base in methanol was added and sufficient time (30 minutes) was allowed for the base to react. Then 2.4 parts of DMS was added, allowed to react and again 1.7 parts of the sodium methylate solution was added, followed by reaction with the final addition of DMS in the amount of 2.3 parts. The unquaternized content in the final product was determined as percent free amine and amine hydrosulfate (% FA & AH) by titrating an aliquot dissolved in IPA plus a trace amount of water, potentiometrically between pH 3.9-10, and calculating the percent FA & AH by a known accepted method using a molecular weight of 725. In accordance with this analysis the final product of this example contained 1.9% FA & AH.

EXAMPLE 2

In this example a series of runs was conducted in which the pH of the quaternized reaction mixture was maintained at a relatively constant pH value on a basic side during the repetitive steps of quaternization and neutralization. The concentration of the dispersion was approximately the same as utilized in Example 1. The procedure involved slowly adding the DMS to the solution of the crude imidazoline at 55°-60° until the pH was slightly lower than desired as judged by testing of wet pH water. A 25% solution of sodium methylate in methanol was added until the pH was back at the desired value. At each stage, sufficient time was allowed for both quaternization and neutralization. The results obtained in terms of percent FA & AH noted for the final products of the various runs together with further details as to the variables observed in the respective runs are set forth in the following table. Run No. 6 represents the standard procedure for carrying out the quaternization reaction in accordance with the prior art.

| RUN NO. | SOLVENT | MOLE DMS/ MOLE AMINE | % FA + AH FINAL | CONSTANT pH |
|---|---|---|---|---|
| 1 | IPA | 1.12 | 1.93 | ∫10 |
| 2 | Diglyme | 1.154 | 2.06 | ∫10 |
| 3 | Glyme | 1.12 | 1.5 | ∫10 |
| 4 | IPA | 1.22 | 1.72 | ∫8 |
| 5 | IPA | 1.19 | 2.74 | ∫8 |

-continued

| RUN NO. | SOLVENT | MOLE DMS/ MOLE AMINE | % FA + AH FINAL | CONSTANT pH |
|---|---|---|---|---|
| 6 | IPA | 0.995 | 8.87 | — |

What is claimed is:

1. A process for quaternizing an imidazoline product provided by the cyclization of a diamidoamine obtained by condensing an ethylene-alkylene triamine and a higher fatty acid or functional equivalent thereof, which comprises the steps: (a) reacting said imidazoline product with a quaternizing agent selected from the group consisting of a lower alkyl halide, a lower dialkyl sulfate, benzyl chloride and benzyl bromide on a basis of about a mole of said agent per mole of the starting amidoamine condensate; (b) basifying the reaction mixture with an alkaline metal alkoxylate to the extent of neutralizing the protonated species formed in step (a); (c) reacting the basified mixture of step (b) with a number of equivalents of quaternizing agent about equal to that of base used in step (b); and sequentially repeating steps (b) and (c) until the non-quaternized content of the reaction mixture is less than about 3 weight percent.

2. A process in accordance with claim 1 wherein the repetitive neutralization steps are conducted so as to maintain the quaternized reaction mixture at a substantially constant pH value within the range of 8–10.

3. A process in accordance with claim 2 wherein said quaternizing agent is dimethyl sulfate.

4. A process in accordance with claim 3 wherein said imidazoline product is obtained by the cyclization of a diamidoamine prepared by condensing tallow with diethylene triamine.

* * * * *